United States Patent [19]

van den Ouweland et al.

[11] 4,134,901

[45] Jan. 16, 1979

[54] FLAVORING SUBSTANCES

[75] Inventors: Godefridus A. M. van den Ouweland, Zevenaar; Henricus G. Peer, Oosterbeek, both of Netherlands

[73] Assignee: Lever Brothers Company, New York, N.Y.

[21] Appl. No.: 718,999

[22] Filed: Aug. 30, 1976

Related U.S. Application Data

[63] Continuation of Ser. No. 599,503, Jul. 28, 1975, abandoned, which is a continuation of Ser. No. 471,424, May 20, 1974, abandoned, which is a continuation-in-part of Ser. No. 838,053, Jun. 27, 1969, Pat. No. 4,020,170.

[30] Foreign Application Priority Data

Jul. 1, 1968 [GB] United Kingdom ............... 31378/68

[51] Int. Cl.$^2$ ...................... C07D 333/16; B02B 3/12
[52] U.S. Cl. ............................ 260/332.3 R; 426/536

[58] Field of Search ...................... 260/347.2, 332.3 R

[56] References Cited

U.S. PATENT DOCUMENTS

| 3,943,260 | 3/1976 | Winter et al. ...................... 260/332.3 |
| 4,020,170 | 4/1977 | Ouweland et al. ............... 260/347.2 |

OTHER PUBLICATIONS

Ouweland et al., Chem. Abst., vol. 72 (1970), p. 90265d.

*Primary Examiner*—A. Siegel
*Attorney, Agent, or Firm*—Melvin H. Kurtz

[57] ABSTRACT

Novel sulphur containing food flavor substances are provided containing an oxygen or sulphur atom in a five-membered ring structure, at least one alkyl group at one of the carbon atoms adjacent to the hetero atom and having a keto oxygen and a hydroxy or mercapto group attached to the other carbon atoms of the ring structure.

4 Claims, No Drawings

FLAVORING SUBSTANCES

This is a continuation of application Ser. No. 599,503, filed July 28, 1975, now abandoned; which is a continuation of Ser. No. 471,424, filed May 20, 1974, now abandoned; which is a continuation-in-part of Ser. No. 838,053, filed June 27, 1969, now U.S. Pat. No. 4,020,170.

The invention relates to food flavouring substances, their preparation and their use in the flavouring of foodstuffs. In particular the invention is concerned with substances capable of imparting a savoury flavour, for example a flavour resembling that of roast, fried or boiled meat, to foodstuffs. The invention furthermore relates to foodstuffs to which such a flavour has been imparted or in which such a flavour is enhanced by judicial incorporation of these flavouring substances.

Flavouring is understood to be the incorporation of compounds having flavouring characteristics per se as well as the incorporation of precursor compounds which do not themselves possess flavouring characteristics but which during the preparation of the foodstuff release or are converted into products having flavouring characteristics.

This application is a continuation-in-part of our U.S. application Ser. No. 838,053 filed June 27, 1969.

It has now been found that certain novel sulphur containing five-membered compounds possess flavour characteristics remarkably similar to that of prepared meat or meat products and which are valuable as food flavouring agents.

The invention provides novel heterocyclic five-membered cyclic compounds which contain a sulphur or oxygen atom in the ring structure, at least one alkyl group at a carbon atom adjacent to the hetero atom, a keto oxygen at another carbon atom and at the remaining carbon atom either a hydroxyl or a mercapto group.

As is apparent from the above, the groups $$-\overset{\parallel}{\underset{O}{C}}-,\ =\underset{\underset{H}{|}}{\overset{|}{C}}-\ \text{and}\ -\overset{\parallel}{\underset{S}{C}}-,\ =\underset{\underset{H}{|}}{\overset{|}{C}}-$$

may be present in the molecules so that keto-enol tautomerism may occur in the compounds involved; consequently the actual compounds will often occur in more than one structure and various systematic names can be given to the compound. Physical data often provide clues as to which structure occurs predominantly and generally these structures and the corresponding systematic names have been used below.

In an embodiment of the invention substances are provided of the formula

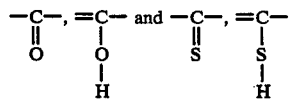

wherein Y represents an oxygen or a sulphur atom and $R_1$ and $R_2$ are selected from the group consisting of hydrogen, methyl and ethyl wherein $R_1$ and $R_2$ cannot both be hydrogen simultaneously. Examples of compounds of this class are:
4-mercapto-5-methyl-2,3-dihydrothiophene-3-one.
4-mercapto-5-methyl-2,3-dihydrofuran-3-one.
4-mercapto-2,5-dimethyl-2,3-dihydrothiophene-3-one.
4-mercapto-5-ethyl-2,3-dihydrofuran-3-one.
4-mercapto-2-ethyl-5-methyl-2,3-dihydrothiophene-3-one.

In another embodiment of the invention compounds of the above formula in which Y represents a sulphur atom and is in the 4-position substituted with a hydroxyl group, are provided. These compounds possess the formula

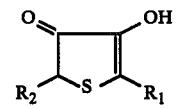

Examples of compounds of this class are:
4-hydroxy-5-methyl-2,3-dihydrothiophene-3-one.
4-hydroxy-2-methyl-2,3-dihydrothiophene-3-one.
4-hydroxy-2,5-dimethyl-2,3-dihydrothiophene-3-one.
2-ethyl-5-methyl-2,3-dihydrothiophene-3-one.

In another embodiment of the invention compounds of the first formula in which the ring is saturated are provided. These compounds including the cis-trans isomers thereof have the formula:

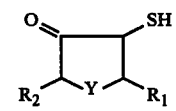

in which Y represents a sulphur or an oxygen atom and $R_1$ and $R_2$ are selected from the group consisting of hydrogen, methyl and ethyl, wherein $R_1$ and $R_2$ cannot both be hydrogen simultaneously. Examples of compounds of this class are:
4-mercapto-5-methyl-tetrahydrofuran-3-one
4-mercapto-5-methyl-tetrahydrothiophene-3-one
4-mercapto-2,5-dimethyl-tetrahydrofuran-3-one
4-mercapto-2-ethyl-tetrahydrothiophene-3-one
4-mercapto-2-ethyl-5-methyl-tetrahydrofuran-3-one.

The above formulae and systematic names have been represented in the form of the most probable tautomeric structure, but the other tautomeric structures are equally comprised by the present invention.

According to the invention substances are provided of a general formula in which each of the carbon atoms 3 and 4 comprises an oxygen atom. These compounds, in which —Y— represents sulphur, possess per se relatively weak flavouring properties but may be converted into compounds having interesting flavouring properties, by reacting with hydrogen sulphide or to some extent when reacting with water.

Excellent food flavouring substances having characteristics similar to those of roast or fried meat are further obtained in case ring carbon atom 4 carries a sulphur atom.

The flavouring characteristics of compounds satisfying the above five general formulae and their tautomers were found to be particularly interesting in case $R^1$ and $R^2$ represent a hydrogen atom or a methyl group.

Flavouring compounds mentioned above can be prepared by various methods, as e.g.

I. A diketo dithioester of the general formula

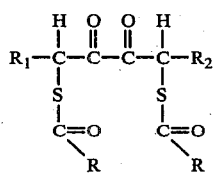

in which R represents an alkyl group, preferably C₂–C₄, can be cyclized into a thiophenone under the influence of protons in an aqueous medium, and the thiophenone isolated.

II. A diketo dithioester, e.g. a ditosylate of the formula

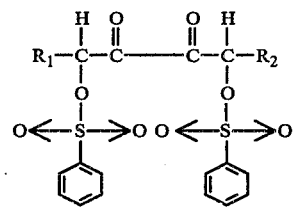

can be cyclized with disodium sulphide in an aqueous medium, and the thiophenone isolated.

III. Cyclic compounds with a sulphur atom attached to a saturated carbon atom are synthesized by reacting the corresponding halogeno compound with potassium thiolacetate in acetone or dimethylformamide and subsequent hydrolysation with sodium methoxide in methanol.

IV. Cyclic compounds with a sulphur atom attached to a saturated carbon atom with less than two double bonds in the ring structure are synthesized by the following reaction path: the corresponding ketone is reduced by Li AlH₄, converted into their p-toluene sulfonic esters and subsequently into the thioacetate. Hydrolysation then yielded the sulphur compound.

V. Cyclic compounds with a sulphur atom attached to an unsaturated carbon atom are synthesized by the reaction of the corresponding ketone with hydrogen sulphide in ethanol saturated with hydrogenchloride and ether at −80° C.

VI. Thioketones or compounds with a sulphur atom attached to an unsaturated carbon atom are obtained by reacting the corresponding ketone with phosphor pentasulphide in toluene at reflux temperature.

A preferred method for preparing mixtures in which several flavouring compounds according to the invention occur is reacting a heterocyclic compound of the structure:

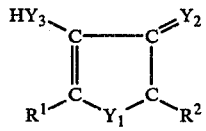

in which Y₁, Y₂ and Y₃ represent oxygen or sulphur atoms of which not more than one represents a sulphur atom, and R¹ and R² represent a hydrogen atom or alkyl group containing 1–2 carbon atoms, with hydrogen sulphide or a hydrogen sulphide liberating compound in the presence of water.

The mixtures thus obtained may further be purified e.g. by removal of hydrogen sulphide or the hydrogen sulphide releasing compound and may be separated into fractions which may possess certain pronounced flavouring characteristics.

Starting materials satisfying the above requirements constitute furanone compounds which may be reacted with hydrogen sulphide such as:
4-hydroxy-5-methyl-2,3-dihydrofuran-3-one
4-hydroxy-2,5-dimethyl-2,3-dihydrofuran-3-one
4-hydroxy-2-methyl-5-ethyl-2,3-dihydrofuran-3-one
4-hydroxy-5-methyl-2-ethyl-2,3-dihydrofuran-3-one
4-hydroxy-2,5-diethyl-2,3-dihydrofuran-3-one
4-acetoxy-5-methyl-2,3-dihydrofuran-3-one
4-methoxy-2,5-dimethyl-2,3-dihydrofuran-3-one.

Of these furanones, the first three named examples are the most preferred. The alkyl substituted furanones which are used according to the present invention can be prepared by heating and reacting a diketo diester of the general formula:

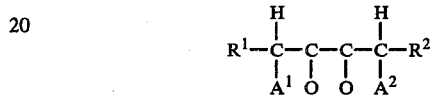

in which R¹ and R² represent a hydrogen atom or an alkyl radical containing 1 or 2 carbon atoms, with the proviso that the number of carbon atoms of R¹ and R² together is at least one and A¹ and R² represent acid radicals. The acid radicals may be derived from carboxylic acids, especially from lower aliphatic carboxylic acids. Preferred ester groups are those derived from acetic and propionic acid.

The reaction is carried out in an aqueous acidic medium which contains at least 50 percent by volume, preferably at least 75 percent, of water, the remainder being a water-miscible polar solvent as, for example a lower aliphatic alcohol such as methanol and ethanol.

The acidic compound available in the aqueous acidic medium may comprise an inorganic acid, a carboxylic acid, or, for example, an organic sulphonic acid. Suitable acids include hydrobromic or hydrochloric acid, sulphuric acid, phosphoric acid, formic acid, acetic acid, propionic acid, p-toluene sulphonic acid and the like. Polycarboxylic acids and hydroxycarboxylic acids are less suitable. The use of strong acids, showing a pH value below 5 or rather below 4, is particularly preferred.

The amount of acid in the aqueous medium is not particularly critical and may vary widely. Good results have been obtained with amounts of 0.1–5 equivalents of acid per liter medium. Also the concentration of the diketo diester in the aqueous medium may vary widely. Generally, less than 200 g of diketo diester are dissolved per liter of medium. For practical reasons, in particular to reduce the volume of the reaction mixture, the use of too dilute solutions is avoided. A practical range is from 10–100 g of diketo diester per liter of medium.

The reaction temperature and time of reaction are related. For convenient reaction periods in the range of 0.5–10, preferably from 1–5 hours, it is preferred to conduct the reaction at temperatures above 75° C., preferably at boiling temperature at atmospheric pressure. It is however possible to obtain a satisfactory conversion at lower temperatures, for example of about 50° C., provided the reaction period is suitably adjusted to at least 20 hours.

After termination of the reaction the aqueous reaction mixture is allowed to cool and the desired furanone derivative is isolated in a conventional way. This could be done, for example, by extraction with ether, drying of the ethereal solution and evaporation of the solvent. Undesired polymeric contaminants are removed by distillation of the product under diminished pressure.

Esterification or etherification of the hydroxyl group in the 4-position may be achieved by conventional methods.

The diketo diester starting materials for the process according to the invention can be prepared in various ways. A convenient method is via acetylenic compounds.

Step 1—Preparation of an alkyne diol.

Acetylene was coupled with two moles of aldehyde using two moles of a Grignard compound. This method is described in Bull. Soc. Chim. — France 425 (1956). Alternatively a 1-alkyne-3-ol could be coupled with formaldehyde as described in Annalen 596 525 (1955) or by coupling a 1-alkyne-3-ol and other aldehydes or ketones (as described in Bull Soc. Chim. supra).

Step 2—Esterification of the alkyne diol.

The diacetates were conveniently prepared by reacting with acetic anhydride in the presence of e.g. pyridine or sodium acetate.

Step 3—Oxidation of the alkyne diester.

The alkyne diester was oxidized with dilute aqueous potassium permanganate at a low temperature yielding the diketo diester. This method has been described in Bull. Soc. Chim. (France) 789 (1949).

Preferred examples of the ketones which may be reacted with hydrogen sulphide according to the invention are:
4-hydroxy-5-methyl-2,3-dihydrofuran-3-one
4-hydroxy-2,5-dimethyl-2,3-dihydrofuran-3-one The sulphur containing compound with which the furanone is reacted is hydrogen sulphide, in the form of a gas, liquid or solution, or an organic or inorganic compound which is capable of liberating hydrogen sulphide, either in gaseous or nacent form, under the reaction conditions.

Suitable examples of organic sulphur-containing compounds are cysteine, or a peptide containing cysteine such as glutathione, cystine mercaptoacetamide, thioacetamide or salts, for example potassium or sodium salts, hydrochlorides, esters or other simple derivatives of these sulphur-containing compounds.

Suitable examples of inorganic sulphur-containing compounds are sulphides or hydrosulphides of alkali metals, alkaline earth metals or ammonia, such as sodium sulphide, potassium sulphide, ammonium sulphide, calcium sulphide or the corresponding hydrosulphides. Also, other inorganic metallic sulphides, for example ferrous sulphide, may be used.

The reaction mixture comprising at least one ketone and hydrogen sulphide or a sulphur-containing compound as herein defined which react to form the flavour substances according to the invention, may optionally also contain other ingredients which improve or enhance the character of the flavour which subsequently is produced. These optional ingredients may be added before, during or after the ketone and hydrogen sulphide or sulphur-containing compound react.

Thus it is possible to include in the reaction mixture amino acids, the preferred amino acids being one or more of the following: arginine, glutamic acid, proline, glycine, α-alanine, β-alanine, threonine, lysine, leucine, iso-leucine, serine, valine, histidine, cysteine and cystine or a salt thereof. Cysteine and cystine may of course serve in the reaction as sulphur-containing compounds according to the invention.

It is also possible to include in the reaction mixture as an optional ingredient a monosaccharide or a carbohydrate which is capable of being hydrolysed to monosaccharide under the conditions of the reaction. The most suitable monosaccharides are hexoses, such as glucose, and pentoses, such as ribose, xylose, rhamnose and arabinose.

It is also possible to conduct the reaction in the presence of a $C_{12}$-$C_{18}$ aliphatic fatty acid, for example palmitic acid or oleic acid or a salt, ester or glyceride thereof.

The proportions of the ketone to hydrogen sulphide or sulphur-containing compound which are present in the reaction mixture may vary widely. Thus it is possible to use proportions on a weight basis of from 1 part ketone and 50 parts hydrogen sulphide or sulphur-containing compound to 50 parts ketone and 1 part hydrogen sulphide or sulphur-containing compound. Preferred weight proportions are between 1 part ketone and 10 parts hydrogen sulphide or sulphur-containing compound to 10 parts ketone and 1 part hydrogen sulphide or sulphur-containing compound.

Where the reaction conditions are such that excess hydrogen sulphide remains after the reaction is complete, it is advisable to allow the reactants to stand, or to apply ventilation or other means to remove the excess hydrogen sulphide, otherwise the flavour substance may be objectionable due to residual hydrogen sulphide.

The reaction should be conducted under conditions in which at least a trace amount of water is present in the reaction mixture; suitably the amount of water present should be at least equal by weight to the amount of hydrogen sulphide or the sulphur-containing compound. It is however preferred for reasons of convenience that the weight of water should be at least equal to that of the reactants, so that intimate mixing of the ingredients is thereby facilitated. In general it is not necessary that the weight of water present should exceed 100 times that of the reactants, primarily to facilitate subsequent concentration of the flavouring substances which are the products of the reaction. It is also possible to conduct the reaction where the water is bound in the form of water of crystallisation. As an example, sodium sulphide nonahydrate may be employed in the reaction to act both as a sulphur-containing compound and as a source of water.

The rate at which the ketone and hydrogen sulphide or sulphur-containing compound react is dependent on the temperature of the reaction mixture, higher temperatures in general resulting in a higher rate of reaction. However, we have found that it is possible to obtain the flavour substances according to the invention by employing a reaction temperature of between 0° and 150° C., but for practical purposes it is preferred and is more convenient to employ a temperature in excess of 60° C., and most preferably between about 90° and 110° C. This is particularly applicable when the reaction is carried out by refluxing at atmospheric pressure.

It is necessary to apply a pressure above that of atmospheric pressure when aqueous systems are heated at a temperature above the boiling point of the system at atmospheric pressure. It has also been found advantageous to employ superatmospheric pressures when one of the reactants is a gas, for example when gaseous hydrogen sulphide is employed.

When the reaction is conducted in the presence of more than a trace amount of water, the pH of the reaction mixture may vary over a wide range of values. The reaction may thus be conducted at pH values ranging from 2 to 10, but values between 4 and 7 are preferred.

The duration of the reaction may vary considerably and is, of course, dependent on other parameters which control the rate of reaction. We have, for example, found that the flavour substances are produced within a few minutes of commencing the reaction and continue to build up in the reaction mixture for several days. As a general guide, we have found that for a reaction temperature of 100° C., a reasonable reaction time is from 1 minute to 15 hours, whereas at room temperature, the flavour composition may be produced in as little as 3 minutes to as long as 30 days. It is, however, preferred to restrict the reaction time to between 1 and 6 hours.

According to a preferred embodiment of the invention, a ketone and a sulphur-containing compound giving rise to hydrogen sulphide are reacted together in the presence of water by boiling or simmering under reflux at a temperature slightly in excess of 100° C. for about 3 hours. The aqueous reaction mixture may subsequently be concentrated to a paste or dried to powder, care being taken to ensure that the loss of volatile components of the flavouring substance so produced is kept to a minimum.

The flavouring substances prepared according to the invention may thus be employed in liquid or semi-liquid form, for example as solutions, emulsions or pastes, or in dried form, for example as a powder. Drying of the reaction products may be accomplished for example by freeze-drying, which has been found to be most suitable for optimum retention of flavour volatiles.

The flavouring substances thus prepared may be blended with a further quantity of a ketone as herein defined, which itself is capable of imparting a savoury taste to a foodstuff, or with one or more compounds from the following classes of substances:

I. Amino acids which may be obtained by hydrolysis, autolysis or fermentation or by a combination thereof from vegetable or animal proteins such as gluten, casein, soyabean protein and the like.

II. Nucleotides, such as adenosine-5'-monophosphate, guanosine-5'-monophosphate, inosine-5'-monophosphate, xanthosine-5'-monophosphate, uridine-5'-monophosphate, cytidine-5'-monophosphate, or their amides, desoxy derivatives or their salts. Combinations of nucleotides, for example guanosine-5'-monophosphate and inosine-5-monophosphate are particularly suitable.

III. Carboxylic acids such as lactic acid, glycolic acid and γ-hydroxy butyric acid on the one hand and dicarboxylic acids such as succinic acid and glutaric acid on the other hand, and especially mixtures of carboxylic acids in which succinic acid and lactic acid occur in weight ratios of 1:30 to 1:150.

IV. Pyrrolidone carboxylic acid or precursors thereof.

V. Peptides such as alanyl-alanine, alanyl-phenylalanine, alanyl-asparagine, carnosine and anserine.

VI. Sweetening substances, both artificial, such as saccharine and cyclamate, and natural, particularly mono- and disaccharides.

VII. Substances with the flavour of cooked or roast meat or of meat broth, (other than those which result from the reaction of a ketone with a sulphur-containing compound as hereinbefore defined), for example the reaction products of amino acids such as cysteine or cystine with reducing sugars, or ascorbic acid, or the reaction products of hydrogen sulphide with lower aliphatic aldehydes and ketones, such as propionaldehyde, crotonaldehyde, methional, mercapto-acetaldehyde.

VIII. Volatile sulphur compounds, such as hydrogen sulphides, mercaptans, disulphides and sulphides, such as dimethyl sulphide and diallyl sulphide.

IX. Guanidines, such as creatine and creatinine.

X. Salts such as sodium chloride, disodium hydrogen phosphate, monosodium dihydrogen phosphate or other alkali or ammonium phosphates and organic phosphates, such as phosphorus-containing amino acids.

XI. Nitrogen-containing compounds, such as ammonia, amines, urea, indole and skatole.

XII. Saturated or unsaturated carboxylic acids, for example those containing from 2 to 12 carbon atoms in the molecule.

XIII. Saturated or unsaturated higher hydroxycarboxylic acids and γ and δ-lactones derived therefrom, such as deca- and dodeca-5-olide and 2,3-dimethyl-2,4-alkadiene-4-olides.

XIV. Lower saturated and unsaturated aldehydes, for example acetaldehyde, propion-aldehyde; iso-butyraldehyde and hepten-4-al.

XV. Lower saturated and unsaturated ketones, such as acetone, butanone and diacetyl.

XVI. Tricholomic acid and biotenic acid or their salts.

XVII. Aromatic and/or heterocyclic compounds, such as ortho amino-acetophenone, N-acetonyl pyrrole, iso-maltol, lenthionine, hypoxanthine, guanine, inosine and guanosine.

XVIII. Lower saturated and unsaturated alcohols, such as ethanol and octanol.

XIX. Colouring substances, such as curcuma and caramel.

XX. Thickening agents such as gelatin and starch.

XXI. Unsaturated $C_{12}$–$C_{18}$ aliphatic fatty acids and their glycerides or saturated glycerides.

The proportions of these optimally added substances used is dependent on the kind of flavour desired and also on the nature of the foodstuff to which they are added together with other ingredients, such as herbs and spices.

In addition to preparing flavouring substances for subsequent addition to foodstuffs, by reaction together a ketone and hydrogen sulphide as herein described, it is also possible to add the unreacted starting materials to the foodstuff so that the flavouring substances may subsequently develop in the foodstuff before consumption. Thus, for example, it is possible to add a ketone and a sulphur-containing compound capable of producing hydrogen sulphide to the ingredients of a soup which is subsequently canned and heat-sterilised. A desirable roast meat-like flavour may thereby be developed within the soup after heat sterilisation in the sealed can.

The flavouring substances prepared according to the invention may otherwise be incorporated into foodstuffs, such as soups, sausage, reformed comminuted meat, simulated meat products, such as textured vegetable protein, and pastry products, in an amount sufficient to impart or enhance the desired flavour. Thus, flavouring amounts will vary according to the individual palate and according to the nature of the foodstuffs. As a general guide, the flavouring substances in amounts of from 1 ppm to 8,000 ppm have been incorporated in foodstuffs, these proportions being expressed on a weight basis.

As an illustration of suitable quantities of the flavouring substances that may be added to specified types of foodstuff, we have found that as little as 1 ppm to 10 ppm w/w is sufficient to impart a pleasant roast meat flavour to soups which are bland or otherwise lightly flavoured. On the other hand, when incorporating a similar roast meat flavour to already flavoured foodstuffs such as those based on vegetable protein, it may be necessary to incorporate larger amounts, for example from 600 to 8,000 ppm w/w of the flavouring substance in order to obtain a desirable flavour. In case a pure compound is added to a foodstuff, from 0.01 to 50 ppm, preferably from 0.1 to 20 ppm (dry matter content) is added.

When the flavour substances prepared according to the invention are added to a foodstuff, it is believed that further reaction in situ in the foodstuff contributes to the development of the desired flavour characteristic. It would thus appear likely, for example, that sulphydryl groupings present in or derived from protein present in the foodstuff react further with the ketone derivatives in the flavour substance to produce compounds having improved flavour properties.

EXAMPLE A1

Preparation of 4-hydroxy-5-methyl-2,3-dihydrothiophene-3-one 140 g of commercially available 1-butyn-3-ol (boiling point 107° at atmospheric pressure) were treated in an aqueous solution with 200 g of a 30% formaldehyde solution in the presence of 10 g CuCl and refluxed for 50 hours. The resulting 156 g (70%) of 2-pentyn-1,4-diol (boiling point 115° C. at 2.5 mm mercury) were isolated by evaporating off the water and distilling the residue.

50 g (0.5 m) of 2-pentyl-1,4-diol were dissolved in 250 ml of dry pyridine. The solution was stirred and cooled to $-10°$ in an ice-salt mixture. With stirring, a cold solution of 286 g (1.5 m) of p-toluene sulfonyl chloride in 550 ml of dry dichloromethane was added dropwise, under exclusion of atmospheric moisture, from the dropping funnel, in such a manner that the temperature did not exceed $-5°$ C. After completion of the addition (about 1.5 hours) stirring at 0° C. was continued for 5 hours, and water (30 ml) was added in portions at intervals of 5 min., with stirring and cooling, so that temperatures did not rise above 5°. The solution was then poured into 1000 ml of cold water. The mixture was extracted three times with dichloromethane; the combined extracts were successively washed with portions of ice-cold dilute sulfuric acid, water, sodium hydrogen carbonate solution and water. The dichloromethane solution was then dried with anhydrous sodium sulphate and evaporated to dryness, affording a syrup which crystallized on standing. It was recrystallized from ethanol; yield 125 g = 61%; m.p. 80–80.5°C.

A solution of the ditosylcompound (89 g = 0.24 m) and potassium thiolacetate (60 g = 0.527 m) in dimethylformamide (1.5 l) was stirred for 45 minutes at 40° C. under nitrogen, then concentrated under reduced pressure and diluted with water (1 liter). The mixture was extracted five times with dichloromethane, the combined extracts were washed with water, dried with anhydrous sodium sulphate and evaporated to dryness.

The residue was distilled through a short-path column, affording 43.8 g = 84.5% of the dithioacetate; bp. 129°–130° at 1.6 mm mercury. $n_D^{20} = 1.5440$. 20 g of the 1,4-dithioacetoxy-2-pentyn were then dissolved in 1000 ml of alcohol-water mixture (90:10 gy volume) and the solution was cooled to $-25°$ C. A solution of 32g potassium permanganate and 48 g magnesium sulphate heptahydrate in 700 ml of water was slowly added in 2 hours whilst maintaining the temperature at $-20$ to $-25°$ C.

The reaction mixture was stirred for another 2 hours at the same temperature, after which 600 g of ice were added. The reaction mixture was then extracted with cold chloroform. The light yellow coloured organic solution yielded after drying and evaporation of the solvent 13.5 g = 59% of a yellow oil (pentane-2,3-dione-1,4-dithioacetate).

10 g of the yellow oil thus obtained (pentane-2,3-dione-1,4-dithioacetate) were dissolved in 1500 ml of 0.5 N aqueous hydrochloric acid and stirred for 1.5 hours at 95° C. After cooling, the reaction mixture was extracted five times with chloroform, the combined extracts were washed with water, dried with anhydrous medium sulphate and evaporated to dryness, affording a syrup which crystallized on standing. After recrystallization, from dichloromethane, white crystals of 4-hydroxy-5-methyl-2,3-dihydrothiophene-3-one were obtained; m.p. 152–153° C.; yield = 40%.

Infra-red absorption characteristics; maxima at 3200, 3000, 2930, 1665, 1615, 1600, 1400, 1368, 1360, 1305, 1190, 1133, 858, 848, 780, 640, 560 cm$^{-1}$. Nuclear magnetic resonance (NMR) data were:

| NMR data: | δ | M |
|---|---|---|
| | a : 2.24 | multiplet 3H |
| | b : 3.60 | multiplet 2H |
| mass data: | m/e i.% | m/e i.% (i. = intensity) |
| | 132 5 | 58.5 |
| | 131 6 | 57 6 |
| | 130 100 | 46 5 |
| | 71 6 | 45 7 |
| | 60 5 | 43 8 |
| | 59 42 | 41 6 |

EXAMPLE A2

Preparation of 4-hydroxy-2,5-dimethyl-2,3-dihydrothiophene-3-one 34.2 g of 3-hexyne-2,5-diol (boiling point 103° at 2 mm mercury) were dissolved in 200 ml of dry pyridine. The solution was stirred and cooled to $-10°$ C. in an ice-salt bath. With stirring, a cold solution of 172 g (0.9 mol) of p-toluene sulfonylchloride in 350 ml of dry dichloromethane was added dropwise (temp. $<-5°$ C.). After completion of the addition (2 hours), stirring at 0° was continued) for 1 hour, and the solution was kept overnight at 0°, with the exclusion of moisture. After addition of water (20 ml) in portions, as described above, and stirring for 30 min., the product was isolated as described above. Recrystallization from dichloromethane/pentane afforded the pure ditosylate with m.p. 118–120°; yield = 101 g (80%).

70 g (0.16 m) of 3-hexyne-2,5-ditosylate were dissolved in a mixture of 1700 ml of ethanol and 750 ml of dioxane. To this solution, which was cooled in ice-water, a solution of 63 g potassium permanganate and 91 g of magnesium sulphate heptahydrate in 1600 ml of water was added at 20–22° C. in the course of 45 min. Stirring was continued for 30 min., 600 ml of water were added and the brown reaction mixture was extracted five times with 200 ml portions of cold chloroform. The combined extracts were washed with water, dried over anhydrous sodium sulphate and evaporated. The solid residue was recrystallized from tetrachloromethane affording 46 g = 64% of yellow crystals with m.p. 128–130° (dec.).

23 g of hexane-3,4-dione-2,5-ditosylate were dissolved in a mixture of 30 ml water and 50 ml ethanol at 90° C. To this solution were added 18 g of sodium sulphide nonahydrate. The mixture was stirred at 90° for 1.5 hours and then diluted with 300 ml water. After acidification with diluted hydrochloric acid, the mixture was extracted five times with dichloromethane. The combined extracts were washed with water, dried over sodium sulphate and evaporated. The crystalline residue was recrystallized from dichloromethane-light petroleum; yield = 4.32 g = 60%, m.p = 77–79° C.

Infra-red absorption characteristics; maxima at 3300, 2980, 2940, 1670, 1600, 1450, 1430, 1395, 1360, 1265, 1130, 1052, 955, 840, 760 cm$^{-1}$.

| NMR data: | δ | | M | | | |
|---|---|---|---|---|---|---|
| | a : 1.55 | doublet | 3H | | | |
| | b : 2.26 | multiplet | 3H | | | |
| | c : 3,70 | multiplet | 1H | | | |
| | d : 5.6 | broad singulet | 1H | | | |
| mass data: (i. = intensity) | m/e i.% | m/e i.% | m/e | i.% | m/e | i.% |
| | 145 10 | 61 12 | 58 | 15 | 45 | 15 |
| | 144 60 | 60 25 | 57 | 19 | | |
| | 85 32 | 59 100 | 55 | 15 | | |

EXAMPLE A3

Preparation of a 4-hydroxy-2-ethyl-5-methyl-2,3-dihydrothiophene-3-one 0.5 mole of 1-butyn-3-ol was coupled with 0.5 mole of propionaldehyde under the influence ethylmagnesium bromide according to Bull. Soc. Chim. (Fr.) 425 (1965) and 3-heptyne-2,5-diol (b.p. 109–110° C. at 2 mm Hg) was obtained in a 64% yield. The alkyne diol was esterified with p-toluene sulfonylchoride as described in Example A1 and 3-heptyne-2,5-ditosylate (m.p. 69.5°–70.5° C.) was obtained in a 76% yield. The alkyne ditosylate was oxidised with aqueous potassium permanganate as described in Example A2 at a temperature of 5° C. and heptane-3,4-dione-2,5-ditosylate was obtained in a 55% yield; m.p. 120–121.5° C. (from tetrachloromethane). 9.36 grams (0.02 m) of heptane-3,4-dione-2,5-ditosylate were dissolved in 200 ml of tetrahydrofuran at 40° C. In the course of 45 min to this solution were added 4.5 grams (0.02 m) of sodium sulphide nonahydrate dissolved in 50 ml of water. The mixture was stirred for 15 minutes at 40° C. and then acidified to pH 5.5. with aqueous hydrochloric acid. The mixture was extracted five times with dichloromethane and the combined extracts were washed with water, dried over sodium sulphate and evaporated. The residue was chromatographed over a polyamide column (50 × 2 cm). Elution with dichloromethane afforded the product in a 40% yield, which was pure according to gaschromatographic analysis.

Infra-red absorption characteristics: maxima at 3350, 2965, 2870, 1670, 1600, 1455, 1435, 1400, 1360, 1280, 1260, 1135, 1060, 1025, 970, 945, 885, 860, 775, 760, 750 cm$^{-1}$.

| mass data: | m/e | i.% | m/e | i.% | (i. = intensity) |
|---|---|---|---|---|---|
| | 158 | 100 | 57 | 65 | |
| | 130 | 80 | 43 | 50 | |
| | 99 | 63 | 41 | 48 | |
| | 85 | 63 | 39 | 43 | |
| | 73 | 100 | | | |
| | 59 | 62 | | | |

EXAMPLE A4

Preparation of 4-mercapto-5-methyl-2,3-dihydrothiophene-3-one and 4-mercapto-5-methyl-2,3-dihydrofuran-3-one A mixture of 2 g of 4-hydroxy-5-methyl-2,3-dihydrothiophene-3-one, 60 ml of liquid hydrogen sulphide and 200 ml of water was placed in an autoclave and the whole was heated at 100° C. for 4 hours. After cooling, the flavouring mixture thus obtained was extracted five times with dichloromethane and the combined extracts were washed and dried over anhydrous sodium sulphate, concentrated to about 10 ml and allowed to stand overnight in the refrigerator. The precipitate formed was collected by filtration, washed and dried to give 0.8 g of starting material.

From the mother liquour 0.5 g of the title compounds were isolated by preparative gaschromatography, using a column of 600 × 0.4 cm, a support of Diatoport S (a silanated silicagel) ex Hewlett Packard loaded with 1% Carbowax 20 M (a polyethylene glycol ether with a molecular weight above 20,000) ex Hewlett Packard and 10% Apiezon (a mixture of stable alkanes) ex Shell Comp. Nitrogen was used as a carrier gas at a velocity of 40 ml per minute. The temperature was programmed; starting temperature 60° C.; increase in temperature 4° per minute. The retention time found for 4-mercapto-5-methyl-2,3-dihydrofuran-3-one was 34.0 minutes and for 4-mercapto-5-methyl-2,3-dihydrothiophene-3-one 53.4 minutes as compared with 27.2 and 32.5 minutes for decane and undecane, respectively.

Infra-red absorption characteristics of 4-mercapto-5-methyl-2,3-dihydrofuran-3-one: maxima at 2920, 2850, 2530 (weak), 1510, 1435, 1375, 1175, 1090, 890, 855, 715 cm$^{-1}$.

| mass data: | m/e | i.% | m/e | i.% | (i. = intensity) |
|---|---|---|---|---|---|
| | 132 | 10 | 96 | 10 | |
| | 131 | 14 | 85 | 14 | |
| | 130 | 100 | 59 | 12 | |
| | 129 | 46 | 52 | 39 | |
| | 98 | 10 | 51 | 36 | |
| | 97 | 51 | 50 | 27 | |
| | | | 45 | 28 | |

Infra-red absorption characteristics of 4-mercapto-5-methyl-2,3-dihydrothiophene-3-one: maxima at 2920, 2860, 2530, 1655, 1565, 1450, 1395, 1375, 1265, 1200, 1150, 1085, 860, 800, 730 cm$^{-1}$.

| mass data: | m/e | i.% | m/e | i.% | m/e | i.% | m/e | i.% |
|---|---|---|---|---|---|---|---|---|
| | 148 | 11 | 114 | 28 | 71 | 25 | 55 | 20 |
| | 147 | 10 | 113 | 35 | 69 | 10 | 53 | 15 |
| | 146 | 100 | 100 | 16 | 61 | 12 | 47 | 10 |
| | 145 | 20 | 99 | 18 | 60 | 25 | 46 | 12 |
| | 132 | 15 | 98 | 13 | 59 | 35 | 45 | 63 |
| | 130 | 40 | 97 | 43 | 58 | 30 | | |
| | 129 | 15 | 85 | 40 | 57 | 10 | | |

EXAMPLE A5

Preparation of
4-mercapto-2,5-dimethyl-2,3-dihydrothiophene-3one 12.8 grams (0.1 m) of 4-hydroxy-2,5-dimethyl-2,3-dihydrofuran-3-one were dissolved in 70 ml of dry pyridine. The solution was stirred and cooled to −10° C. in an ice-salt bath. With stirring a cold solution of 22.9 grams (0.12 m) of p-toluene sulfonylchloride in 50 ml of dry dichloromethane was added dropwise (temp. below −5° C.). After completion of the addition (1 hour), stirring at 0° C. was continued for 3 hours, and water (10 ml) was added in portions at intervals of 5 min., with stirring and cooling, so that the temperature did not rise above 5° C. The solution was then poured into 250 ml of ice-water. The mixture was extracted four times with dichloromethane, and the combined extracts were successively washed with portions of ice-cold dilute sulphuric acid, water, sodium hydrogen carbonate solution and water. The dichloromethane solution was then dried with anhydrous sodium sulphate and evaporated to dryness. Crystallization from ethanol yielded 21.3 grams = 75.5% of the pure 4-p-toluenesulfonyloxy-2,5-dimethyl-2,3-dihydrofuran-3-one with m.p. 70°–72° C. 3.5 grams (12.4 mmol) of the tosylate thus obtained were dissolved in a mixture of 15 ml of ethanol and 5 ml of water at 40° C. To this solution was added a solution of 1.68 grams (30 mmol) of sodium hydrogen sulphide in 20 ml of ethanol, while a gentle stream of hydrogen sulphide was passed through the reaction mixture. After completion of the addition, which took one hour, stirring and passing of $H_2S$ into the solution were continued for 6 hours at 40° C. and the reaction mixture was diluted with 200 ml of water, acidified with aqueous dilute hydrochloric acid (pH 5.5) and continuously extracted with ether for 18 hours. The extract was dried over anhydrous sodium sulphate and evaporated to dryness. From the residue the title compound was isolated in a quantity of 3 grams by preparative gas-chromatography, using a column of 600 × 0.4 cm, a support of Diatoport S (a silanated silicagel) ex Hewlett Packard, loaded with 1% Carbowax 20 M (a polyethylene glycol ether with a molecular weight above 20,000) ex Hewlett Packard and 10% Apiezon (a mixture of stable alkanes) ex Shell Comp. Nitrogen was used as a carrier gas at a velocity of 40 ml per minute. The temperature was programmed; starting temperature 60° C.; increase in temperature 4° per minute. The retention time found for 4-mercapto-2,5-dimethyl-2,3-dihydrothiophene-3-one was 40.1 minutes.

Infra-red absorption characteristics of 4-mercapto-2,5-dimethyl-2,3-dihydrothiophene-3-one: maxima at 2980, 2920, 2860, 2530, 1670, 1565, 1460, 1390, 1375, 1275, 1255, 1130, 1000, 930, 875, 770, 740 and 540 cm$^{-1}$.

| mass data: | m/e | i.% | m/e | i.% | m/e | i.% |
|---|---|---|---|---|---|---|
| | 162 | 12 | 111 | 25 | 67 | 26 |
| | 160 | 100 | 99 | 26 | 61 | 31 |
| | 159 | 10 | 85 | 18 | 60 | 34 |
| | 127 | 26 | 72 | 30 | 59 | 95 |
| | 117 | 17 | 71 | 30 | 58 | 25 |
| | | | | | 57 | 28 |

EXAMPLE A6

Synthesis of
2,5-dimethyl-4-mercapto-2,3-dihydrofuran-3-one

To a solution of 6.4 g (0.05 mole) in 300 ml of glacial acetic acid were added 37.5 ml of benzylmercaptan and 5 ml of concentrated hydrochloric acid. The mixture was maintained at room temperature for 24 hours. Upon evaporation of the reaction mixture 7.5 g of a yellow oil remained. Distillation of the oil yielded 3.7 g of 2,5-dimethyl-3-phenylthio-2,3-dihydrofuran-3-one, b.p. 130–132 at 0.3 mm.

Infra-red absorption characteristics in $CCl_4$: maxima at 3040, 2990, 2940, 2710, 1595, 1500, 1460, 1430, 1395, 1350, 1290, 1120, 1040, 988, 700 cm$^{-1}$.

| mass data: | m/e | i.% | m/e | i.% | (i. = intensity) |
|---|---|---|---|---|---|
| | 123 | 23 | 77 | 19 | |
| | 106 | 13 | 65 | 17 | |
| | 105 | 13 | 51 | 12 | |
| | 92 | 15 | 45 | 18 | |
| | 91 | 100 | 43 | 64 | |

A solution of 2.7 g (11.5 mmole) of the above prepared benzylmercaptal in 75 ml of anhydrous ether was added at −50° C. to 30 ml of liquid ammonia. To the so obtained mixture 1.1 g of sodium in small pieces were added over a period of 1 hr and the mixture was then stirred for 15 minutes. After careful dropwise addition of 4 ml of absolute ethanol, the mixture was poured cautiously into 100 ml of ice water. Acidification to pH 6 with acetic acid followed by ether extraction produced 1.7 gram of residue, from which the title compound could be isolated by preparative gas-chromatography. Relative retention time as compared with 43.1 minutes found for dodecane was 41.1 minutes.

Infra-red absorption characteristics in $CCl_4$: maxima at 2990, 2840, 2560, 1713, 1612, 1583, 1450, 1395, 1377, 1350, 1291, 1168, 1115, 1065, 1050, 980, 660, 610, 542 cm$^{-1}$.

| mass data: | m/e | i.% | m/e | i.% |
|---|---|---|---|---|
| | 144 | 55 | 45 | 26 |
| | 102 | 20 | 43 | 100 |
| | 101 | 58 | 41 | 8 |
| | 72 | 14 | | |
| | 71 | 17 | | |
| | 68 | 10 | | |
| | 55 | 8 | | |

EXAMPLE A 7

Synthesis of
2,5-dimethyl-4-mercaptotetrahydrofuran-3-one

A solution of 936 mg of 2,5-dimethyl-4-benzylthio-2,3-dihydrofuran-3-one (cf. Example A6) in 50 ml of anhydrous ether was added dropwise to a stirred solution of 670 mg of sodium in 30 ml of liquid ammonia. An additional 670 mg of sodium was added over a period of 1 hr and the mixture was then stirred for 2 hours. After addition of 5 ml of absolute ethanol, the mixture was poured into water, acidified with acetic acid, and extracted with chloroform. Evaporation of the solvent gave 440 mg of a light yellow oil from which the title compound could be isolated by preparative gas-chromatography.

Relative retention time as compared with 43.1 minutes found for dodecane was 22.6 minutes.

Infra-red absorption characteristics in CCl$_4$: maxima at 2990, 2940, 2880, 2570, 1775, 1453, 1395, 1380, 1340, 1288, 1220, 1157, 1120, 1090, 1010, 930, 857, 690, 505 cm$^{-1}$.

| mass data: | m/e | i.% | m/e | i.% |
|---|---|---|---|---|
| | 102 | 83 | 55 | 19 |
| | 74 | 100 | 45 | 22 |
| | 73 | 8 | 43 | 27 |
| | 69 | 18 | 42 | 9 |
| | 57 | 15 | 41 | 85 |

EXAMPLE A8

Synthesis of 2,5-diethyl-4-mercapto-2,3-dihydrofuran-3-one 7.8 g (0.05 mmol) of 2,5-diethyl-4-hydroxy-2,3-dihydrofuran-3-one were converted via its benzylmercaptal into the title compound according to the method described in Example A6. From the reaction product the title compound was isolated by preparative gaschromatography.

Relative retention time as compared with 43.1 minutes for dodecane was 57.6 minutes.

Infra-red absorption characteristics in CCl$_4$: maxima at 2970, 2940, 2880, 2550, 1708, 1600, 1466, 1390, 1370, 1160, 1013, 942 cm$^{-1}$.

| mass data: | m/e | i.% | m/e | i.% | (i. = intensity) |
|---|---|---|---|---|---|
| | 172 | 60 | 55 | 17 | |
| | 157 | 24 | 53 | 22 | |
| | 115 | 43 | 45 | 33 | |
| | 71 | 19 | 43 | 28 | |
| | 57 | 100 | 41 | 16 | |

EXAMPLE A9

Synthesis of 2,5-diethyl-4-mercaptotetrahydrofuran-3-one

A solution of 1.4 g of 2,5-diethyl-4-benzylthio-2,3-dihydrofuran-3-one in 50 ml anhydrous ether was treated with 0.88 g of sodium in liquid ammonia as described in Example A7. After working up the reaction mixture the title compound could be isolated by preparative gaschromatography. Relative retention time as compared with 43.1 minutes for dodecane was 51.9 minutes.

Infra-red absorption characteristics in CCl$_4$: maxima at 2970, 2940, 2880, 2560, 1770, 1468, 1390, 1340, 1200, 1150, 1070, 990, 940, 902, 715 cm$^{-1}$.

| mass data: | m/e | i.% | m/e | i.% | (i. = intensity) |
|---|---|---|---|---|---|
| | 116 | 75 | 60 | 31 | |
| | 102 | 30 | 55 | 100 | |
| | 88 | 62 | 54 | 39 | |
| | 74 | 77 | 45 | 28 | |
| | 73 | 42 | 41 | 45 | |

EXAMPLE B1

4-hydroxy-5-methyl-2,3-dihydrofuran-3-one (0.5 g) was dissolved in water (30 ml) and reacted with hydrogen sulphide (15 g) for 4 hours at 95–100° C. in a glass-lined autoclave. At the end of the reaction period the mixture was cooled and poured into ice-water (100 ml) and extracted five times with dichloromethane. The combined extracts (125 ml) were concentrated at atmospheric pressure to 10 ml and the concentrated dichloromethane extract was analysed by gas-liquid chromatography on a 600-0,4 cm glass column with Diatoport S as support. The stationary phase was Apiezon L 10% and Carbowax 20 M 1%, the temperature was programmed from 60°–220° C. at 4° C./min, the carrier gas was nitrogen with a velocity of 40 ml/min and the recorder speed was 48 cm/h. From the exhaust of the gaschromatograph the various microgram samples could be trapped and their infra-red spectra could be obtained from these samples according to the method described by H. Copier and J. H. v.d. Maas, Spectro Chemica Acta, 23A 2699 (1967).

The infra-red spectra were determined using a Perkin-Elmer 225 and 257 spectrometer. The mass data were determined using an A.E.J. MS-9 instrument at a source temperature of 200° C. with the following procedure: On one of the inlets of the mass spectrometer a capillary with 0.1 ml/minute conductance was mounted. The glass tubes with the absorbed eluent were connected to this capillary by a ground glass joint, a heater was placed around the sample tube and with a stream of helium the compound was flushed into the ion source of the mass spectrometer.

From the reaction mixture the following products were isolated and identified:

| Mass data m/e and intensity % | Infra-red data (cm$^{-1}$) | Ret. Time min. *) | Assumed Structure | |
|---|---|---|---|---|
| 114 (100), 113 (50), 85 (60), 71 (45), 69 (36), 59 (35), 53 (44), 51 (41), 45 (56), 43 (85) | 2950, 2920, 2850, 1585, 1560, 1518, 1510, 1440, 1387, 1225, 1195, 1123, 1088, 1018, 940, 888, 730 | 26.6 |  | a |
| 116 (70), 84 (22), 83 (20), 73 (26), 71 (19), 60 (24), 45 (55), 43 (100), 42 (20), 41 (20), | 2960, 2920, 2890, 2860, 1740, 1663, 1635, 1480, 1435, 1400, 1380, 1365, 1220, 1060, 1030, 980, 960, 905, 680 | 30.6 | 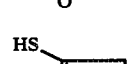 | b |
| 116 (17), 55 (11), 42 (50), 73 (13), 45 (32), 41 (26), 72 (22), 43 (100), 39 (25), 71 (34) | 2980, 2930, 2862, 2540, 1620, 1455, 1385, 1270, 1235, 1110, 1080, 1050, 1035, 945, 899, 825, 650 | | 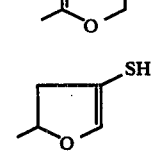 | c |

-continued

| Mass data m/e and intensity % | Infra-red data (cm$^{-1}$) | Ret. Time min.*) | Assumed Structure | |
|---|---|---|---|---|
| 84 (30), 55 (40) 74 (100), 46 (30) 73 (20), 45 (80) 59 (20), 43 (90) 56 (25), 41 (100) | 2975, 2930, 2870 2540, 1453, 1385, 1355, 1195, 1140, 1120, 1075, 1080, 860 | 25.5 |  | d |
| 84 (30), 55 (40) 74 (100), 46 (30) 73 (20), 45 (80) 59 (20), 43 (90) 56 (25), 41 (100) | 2975, 2930, 2870 2540, 1453, 1385 1355, 1320, 1110 1070, 1020, 990, 850 | 29.2 | trans 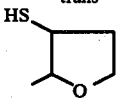 | e |
| | | 27.3 | cis 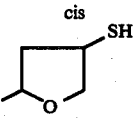 | f |
| 85 (46), 54 (21) 73 (33), 47 (20) 60 (20), 45 (48) 59 (17), 43 (72) 55 (100), 41 (100) | 2970, 2925, 2860, 2540, 1440, 1380, 1350, 1080, 1015 890, 810 | 27.7 | trans 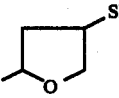 | g |
| 132 (20), 117 (100), 100 (12), 99 (12), 85 (25), 59 (40), 58 (14), 45 (30), 43 (12), 41 (27) | | 37.5 | cis 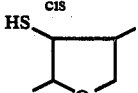 | h |
| 133 (62), 130 (60), 129 (55), 117 (47), 97 (65), 85 (55), 60 (67), 59 (94), 43 (35), 41 (52) | | 40.7 | 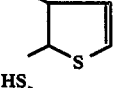 | i |
| 132 (48), 131 (41), 103 (31), 97 (58), 71 (45), 67 (35), 59 (35), 45 (85), 43 (100), 41 (53) | | 42.5 | 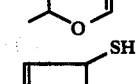 | j |
| 132 (48), 131 (41), 103 (31), 97 (58), 71 (45), 67 (35), 59 (35), 45 (85), 43 (100), 41 (53) | 2960, 2910, 2850, 1725, 1645, 1420, 1378, 1255, 1115, 940, 780 | 48.1 | 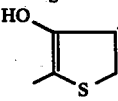 | k |
| Corresponding to data of Example A1 | | 47.0 | 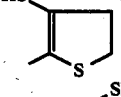 | l |
| 132 (100), 98 (28), 65 (19), 131 (29), 97 (34), 59 (70), 99 (90), 71 (23), 58 (18), 45 (41) | 2960, 2930, 2910, 2840, 1585, 1435, 1400, 1375, 1300, 1265, 1149, 1020, 850, 750, 685, 675 | 48 | 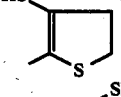 | m |
| 132 (100), 84 (36), 117 (95), 59 (38), 99 (58), 58 (28), 97 (38), 45 (100), 85 (37), 41 (42) | 2960, 2920, 2860, 2510, 1540, 1445, 1425, 1400, 1375, 1260, 1205, 1080, 930, 825, 790, 720, 680 | 43.1 | 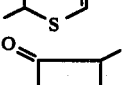 | n |
| 148, 115, 92, 74, 59 | | 42.1 | 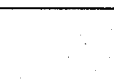 | o |

*)As compared with 43.1 min. for dodecane.

EXAMPLE B2

4-hydroxy-2,5-dimethyl-2,3-dihydrofuran-3-one (0.5 g) was treated with hydrogensulphide (15 g) and analysed as described in Example B1. From the reaction product the following components were isolated and identified:

| Mass data | Infra-red data | Ret. Time min.*) | Structure | |
|---|---|---|---|---|
| 129(45),95(10), 128(65),85(25), 127(22),45(100), 113(8),43(100), 96(45),39(9) | 3115,2950,2920, 2880,2850,1567, 1430,1380,1365, 1330,1225,1115, 1065,1000,980, 920,795,646,615 | 42 | 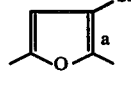 | a |
| 130(14),55(10), 43(100),88(10), 53(14),41(13), 87(12),45(20), 39(14),71(24), | 2975,2925,2862, 2540,1610,1460, 1450,1378,1330, 1262,1218,938 875,830 | 28.5 | 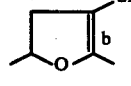 | b |

-continued

| Mass data | Infra-red data | Ret. Time min.*) | Structure |
|---|---|---|---|
| 99(26),73(26), 43(53),98(19), 60 (24),39(14), 88(50),55(100), 83(8),45(18), | 2975,2930,2870, 2540,1458,1448, 1380,1165,1125, 1100,1083,951, 916,880 | 29.0 | 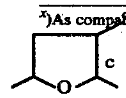 |
| Identical with data of Example A2 | | 54.4 | 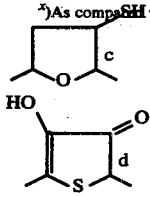 |
| 146,112,102 74,55,45,43, 41 | 2990,2945,2875,2570, 1775,1462,1452,1396, 1379,1370,1348,1288, 1220,1157,1120,1090, 1013,930,856,505 | 22.6 | 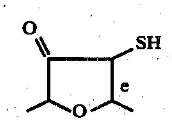 |
| | | | 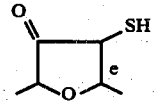 |

*)As compared with 43.1 min. for dodecane.

EXAMPLE B3

4-hydroxy-5-methyl-2,3-dihydrothiophene-3-one (0.5 g) was treated with hydrogen sulphide (15 g) as described in Example B1. From the reaction product the following reaction components were isolated.

| Mass data | Infra-red data | Ret. time min.*) | Structure |
|---|---|---|---|
| 134 (100), 49 (88), 86 (42), 45 (45), 85 (46), 43 (46), 84 (62), 41 (52), 61 (36), (59 (38) | 2958, 2920, 2860, 2540, 1450, 1435, 1375, 1268, 1205, 1182, 1030, 1000, 940, 735, 715, 700 | 40.5 | a |
| cis-compound 134 (32) 85 (19) 74 (38) 69 (20) 59 (27) 55 (28) 47 (28) 45 (52) 41 (100) 39 (47) | trans-compound 134 (82) 74 (70) 69 (54) 67 (35) 59 (26) 55 (48) 47 (26) 45 (36) 41 (100) 39 (45) | cis: 2962, 2920, 2895, 2865, 1456, 1442, 1376, 1315, 1260, 1200, 1170, 1020, 960, 680 trans: 2962, 2925, 2880, 2850, 1450, 1440, 1379, 1330, 1270, 1200, 670 | cis 41.6 trans 43.8 | b |
| Corresponding to data of Example A4 | | 34++ | c |
| Corresponding to data of Example A4 | | 53.4++ | d |
| 116, 115, 84, 73, 42 | | 26.2+ | e |

*)As compared with 27.2 minutes for decane.

EXAMPLE B4

4-hydroxy-2,5-dimethyl-2,3-dihydrothiophene-3-one (0.5g) was treated with hydrogen sulphide (15 g) as described in Example B1. From the reaction product the following components were isolated.

| Mass data | Infra-red data | Ret. time min.* | Stucture |
|---|---|---|---|
| 144 (60), 143 (36), 114 (27), 113 (21), 111 (52), 99 (59), 59 (100), 55 (29), 45 (55), 41 (23) | 2958, 2920, 2860, 1445, 1378, 1315, 1190, 1153, 1132, 822, 680, 625 | 44.5 | a |
| 146 (90), 61 (25), 131 (44), 59 (100), 113 (60), 45 (55), 98 (38), 41 (28), 85 (24), 39 (36), | 2960, 2920, 2882, 2837, 1450, 1440, 1290, 1250, 1210, 1152, 1015, 1000, 688 | 43.1 | b |
| cis-compound 148 (36) 99 (33) 67 (40) 61 (90) 60 (39) 59 (70) 55 (100) | trans-compound 148 (48) 99 (29) 67 (46) 61 (88) 60 (39) 59 (67) 55 (100) | cis: 2965, 2925, 2865, 1458, 1450, 1380, 1310, 1250, 1168, 1025, 1000, 992, 680 trans: 2965, 2920 2860, 1455, 1448, 1378, 1270, 1190, 1168, 1020, 997, 985 | cis 42.4 trans 44.7 | c |
| Corresponding to data of Example A5 | | | d |

*As compared with 43.1 min. for dodecane.

EXAMPLE C1

A beef-flavoured composition was prepared by adding 250 ml of water to a mixture of 5.7 g of 4-hydroxy-5-methyl-2,3-dihydrofuran-3-one and 25.0 g of cysteine and heating the mixture at about 100° C. for 2½ hours.

The resulting mixture was cooled and quantities of between 0.2 and 2.0 ml of the reaction mixture were sprayed over 100 g portions of dehydrated textured vegetable protein containing no meat. An excellent roast meat flavour was thereby imparted to this material as assessed by eleven out of a total panel of twelve expert tasters.

Dextrin-maltose was added to a portion of the flavoured mixture which resulted from the reaction described above in an amount which provided a composition containing about 70 parts by weight of dextrin-maltose to each part of the substance calculated on a solid basis. The composition was freeze-dried and a beef-flavoured product was obtained.

EXAMPLE C2

To 6.4 g of 4-hydroxy-2,5-dimethyl-2,3-dihydrofuran-3-one in a buffer solution containing about 35 g sodium acetate, about 14 g of acetic acid and 400 ml of water (pH 5.0), a solution of 12 g of sodium sulphide ($Na_2S.9H_2O$) in 200 ml of water was added over a period of 30 minutes. The mixture was then boiled under reflux condictions at atmospheric pressure for 2 hours and allowed to cool. The pH then was 6.6 The reaction mixture so obtained had a good roasted-meat flavour.

EXAMPLE C3

3.0 g of a 70/30 mixture of 4-hydroxy-2-methyl-5-ethyl-2,3-dihydrofuran-3-one and 4-hydroxy-5-methyl-2-ethyl-2,3-dihydrofuran-3-one, 9.0 g of cysteine and 60 ml of water were heated in a round-bottomed flask fitted with reflux condenser for 2 hours at 100° C. The reflux condenser was then removed and the contents cooled to room temperature. The resulting solution had a good roasted-meat flavour.

EXAMPLE C4

A composition with a meat-like flavour was prepared by adding 100 ml of water to a mixture of 4.0 g of 4-hydroxy-2,5-diethyl-2,3-dihydrofuran-3-one and 20.0 g of cysteine and heating the mixture at 95°-100° C. for 4 hours.

EXAMPLE C5

A mixture of 1.5 g of 4-hydroxy-5-methyl-2,3-dihydrofuran-3-one and 1.5 g of cysteine in 30 ml of water was heated at about 100° C. for 2½ hours. To the resulting solution were added 33 g of malto-dextrin. The solution thus obtained was carefully freeze-dried. The powder obtained was used as a good beef flavour in soup or gravy.

EXAMPLE C6

5.0 g of 4-hydroxy-2,5-dimethyl-2,3-dihydrofuran-3-one, 0.5 g of hydrogen sulphide and 100 ml of water were placed in an autoclave and heated for 2 hours at 100° C. To the resulting solution were added 100 g of malto-dextrin. The solution thus obtained was carefully freeze-dried. The powder obtained was used as a beef flavour in soup.

EXAMPLE C7

1.6 g of 4-hydroxy-2,5-dimethyl-2,3-dihydrofuran-3-one, 8.0 g of glutathione and 50 ml of water were heated for 1½ hours at 100° C. in a round-bottomed flask fitted with a reflux condenser. To the resulting solution were added 5.0 g cysteine, and the mixture was again heated for 2 hours at 100° C. The resulting solution had a good roasted-meat flavour.

EXAMPLE C8

A mixture of 4 g of powdered casein hydrolysate, 2 g of cysteine, 1 g of xylose, 1 g of 4-hydroxy-5-methyl-2,3-dihydrofuran-3-one and 50 ml of water was heated in a flask with stirring for 2½ hours at 95° C. The solution thus obtained proved to have a good beef flavour.

EXAMPLE C9

A mixture of 5 g 4-hydroxy-5-methyl-2,3-dihydrothiophene-3-one (cf. Example A1), 0.5 g of hydrogen sulphide and 50 ml of water was heated in an autoclave for 4 hours at 100° C. and was subsequently allowed to cool. A product with a roasted-meat flavour was obtained which was diluted to a volume of 1 liter, forming a liquid meat flavour.

EXAMPLE D1

A dry goulash soup was prepared by mixing the following ingredients:

|  | grams |
| --- | --- |
| Dried meat | 5 |
| Salt | 8 |
| Monosodium glutamate | 2 |
| Protein hydrolysate | 1 |
| Dried onion | 5 |
| Toasted onion | 5 |
| Tomato powder | 4 |
| Paprika powder | 3 |
| Beef tallow | 10 |
| Corn starch | 25 |
| Herbs and spices | 4. |

According to this recipe two portions were prepared; each portion was used to make one liter of goulash soup by boiling it with 1 l of water for 20 minutes. To the first portion 0.5 ml of ethanol were added, whereas to the second portion 0.5 ml of ethanol containing 5 mg 3-mercapto-2-methyl-tetrahydrofuran (cf. Example A7) were added. Both soups were compared by a panel consisting of 12 persons. The majority of the panel preferred the soup in which the 3-mercapto-2-methyl-tetrahydrofuran had been incorporated. The panel indicated as the reason for this preference the more pronounced meat-like flavour of the relevant product.

EXAMPLE D2

A gravy was prepared from the following ingredients:

|  | grams |
| --- | --- |
| Potato starch | 30 |
| Onion powder | 5 |
| Monosodium glutamate | 6 |
| Tallow | 40 |
| Wheat flour | 30 |
| Caramel dye | 3.2 |
| Pepper | 0.04 |
| Bay leaf | 0.04 |
| Clove | 0.04 |
| Salt | 16 |
| Protein hydrolysate | 8 |
| Commercial meat extract powder | 4 |
| Tomato powder | 2 |

The tallow was molten and potato starch and wheat flour were added with continuous stirring. Subsequently the remaining ingredients were well mixed and also added and the mixture was made up with water to a volume of 2 liters and boiled for 10 minutes.

The gravy thus obtained was divided into two equal parts and to the first part a solution of 10 ml of water containing 10 mg of 4-hydroxy-2,5-dimethyl-2,3-dihydrothiophene-3-one (cf. Example A2) were added, whereas to the other part 10 ml of water were added.

After mixing, both samples were tested by a panel consisting of 9 persons of which 8 preferred the sample containing the thiophene derivative.

EXAMPLE D3

A paprica meat sauce was prepared from the following ingredients:

|  | grams |
|---|---|
| Fresh red paprica, chopped | 80 |
| Paprika powder | 12 |
| Onion, comminuted | 100 |
| Tomato puree | 30 |
| Salt | 15 |
| Pepper | 1 |
| Garlic powder | 0.1 |
| Hydrogenated animal fat | 30 |
| Wheat flour | 60 |
| Meat | 250 |
| Water up to | 1000 |

The meat was fried in the fat and the onion and paprika were added and stewed in the mixture. Subsequently 200 g of water and the remaining ingredients, with the exception of wheat flour, were added and heated up to the boil. The wheat flour was mixed with another 200 g of water and this was added to thicken the sauce. The remainder of the water was then added.

The meat sauce thus obtained was divided into two equal parts, and to one of the samples 10 ml of water, in which 10 mg of 4-hydroxy-2,5-dimethyl-2,3-dihydrothiophene-3-one (cf. Example A2) were dissolved, were added, whereas to the other sample 10 ml of pure water were added. Both sauces were tested by a panel consisting of 9 persons of which the majority preferred the sample containing the thiophene derivative.

EXAMPLE D4

A chicken soup mix was prepared with the following ingredients:

|  | grams |
|---|---|
| Salt | 3 |
| Monosodium glutamate | 2 |
| Sucrose | 1 |
| Meat extract | 5 |
| Protein hydrolysate | 2.5 |
| Chicken powder | 3 |
| Chicken fat | 5 |
| Pieces dry chicken | 2 |
| Noodles | 30 |
| Dried parsley | 0.3 |
| Mixed spices | 2 |

This mixture was used for preparing approximately one liter of chicken soup by bouling it with one liter of water for ten minutes.

The soup thus obtained was divided into two portions. To the first portion 2 ml of the flavouring mixture prepared according to Example A1 were added. Both soups were compared by a panel consisting of 12 persons of which the majority preferred the soup flavoured according to the invention.

EXAMPLE D5

A gravy was prepared from the following ingredients:

|  | grams |
|---|---|
| Potato starch | 15 |
| Onion powder | 2.5 |
| Monosidium glutamate | 3 |
| Beef tallow | 20 |
| Flour | 15 |
| Caramel | 1.6 |
| Pepper | 0.02 |
| Bay leaves | 0.02 |
| Clove | 0.02 |
| Sodium chloride | 8 |
| Protein hydrolysate | 4 |
| Beef extract powder | 2 |
| Tomato powder | 1 |
|  | 72.16 |

The potato starch and flour were added to the molten beef tallow at 60° C. with continuous stirring. The other ingredients were well blended and likewise added to the beef tallow. The whole mixture was boiled in 1 liter of water.

The gravy so obtained was divided into two portions of 500 ml. In the first portion 250 mg of malto-dextrin was dissolved; in the second portion 250 mg of the flavour powder prepared according to Example C5. Both gravies were assessed in a paired comparison test by a panel consisting of 12 persons.

The gravy containing the flavour powder was preferred by 10 out of the 12 tasters because of its more pronounced fried-meat flavour.

EXAMPLE D6

A basic composition for a dry beef soup was obtained by mixing the following ingredients:

|  | grams |
|---|---|
| Onion powder | 0.5 |
| Spice mix | 0.5 |
| Fat | 4 |
| Dried soup vegetables | 1 |
| Monosodium glutamate | 2 |
| Modified potato starch | 3 |
| Noodles | 20 |
| Salt | 8 |

One liter of water was added to the mixture and the whole was boiled for 5 minutes. The soup so obtained was divided into two portions of 500 ml. In the first portion 150 mg of malto-dextin was dissolved and in the second portion 150 mg of the flavour powder prepared according to Example C5.

Both soups were assessed in a paired comparison test by a panel consisting of 8 persons. The soup containing the flavour powder had a characteristic beef flavour and was preferred by 7 out of the 8 tasters.

EXAMPLE D7

1 liter gravy was prepared according to the method described in Example D5. This gravy was divided into two portions of 500 ml each. To the first portion 125 mg of malto-dextrin were added and to the second portion 125 mg of the flavour powder prepared according to Example C6. Subsequently both gravies were boiled for 5 minutes and judged afterwards by a panel consisting of 9 expert tasters. Of these, 7 persons preferred the gravy with the aroma powder while the other 2 expressed no preference. A fuller flavour and a more meaty taste were given as reasons for the preference.

EXAMPLE D8

Minced meat was prepared from the following ingredients:

|              | grams |
|--------------|-------|
| Sausage meat | 825   |
| Salt         | 10    |
| Whole egg    | 82.5  |
| Bread-crumbs | 82.5  |
|              | 1000  |

The minced meat so obtained was divided into two portions of 500 g each. To the first portion was added a mixture of 10 g of bread-crumbs and 0.25 g malto-dextrin, and to the second portion a mixture of 10 g of bread-crumbs and 0.25 g of the flavour powder prepared according to Example C6. Meat balls prepared from each portion were fried in margarine for 30 minutes. The meat balls of both portions were assessed in a paired comparison test by a panel consisting of 8 persons. A unanimous preference was shown for the meat balls containing the flavour powder, because of the more pronounced fried meat flavour.

EXAMPLE D9

A basis for canned beef soup was prepared by adding the following ingredients to 4 liters of water:

|                      | grams |
|----------------------|-------|
| Noodled              | 160   |
| Herbs and spices     | 1.6   |
| Tallow               | 80    |
| Vegetables           | 400   |
| Monosodium glutamate | 16    |
| Protein hydrolysate  | 16    |
| Meat extract         | 16    |
| Salt                 | 64    |
| Raw meat             | 400   |

The total amount was divided into two portions, each of 2 liters. 1.4 g of the flavoured solution prepared according to Example C7 was added to one of the portions. The second portion, which was used without further addition, served as a control. The mixtures thus obtained were canned in half-liter tins and sterilised in an autoclave. A soup ready for consumption was prepared by adding an equal volume of water to the contents of each tin. After heating, both soups were served to a panel consisting of 19 persons for organoleptic testing. The soup with the flavour solution was preferred by 15 persons, because of its more pronounced meaty flavour.

EXAMPLE D10

One liter of gravy was prepared according to the method described in Example D5. This gravy was divided into two portions of 500 ml each. To one of the portions was added 0.2 g of the flavoured solution obtained in Example C7, while the other portion was used without further addition. Both gravies were judged by a panel consisting of 9 persons. Of these panel 8 persons preferred the gravy with the flavour solution. A more pronounced meaty taste and a fuller flavour were given as reasons for the preference.

EXAMPLE D11

One liter of gravy was prepared according to the method described in Example D5. This gravy was divided into two portions of 500 ml each. To the first portion was added 0.5 g of the flavoured solution prepared according to Example C8, and to the second portion, 0.5 g of a solution prepared according to the method described in Example C8, except that the 1 g of 4-hydroxy-2,3-dihydrofuran-3-one had been omitted. Both gravies were assessed in a paired comparison test by a panel consisting of 9 persons. The gravy portion containing the flavoured solution prepared, using all the ingredients of Example C8, was significantly preferred because of its more pronounced meat flavour.

EXAMPLE D12

One liter of gravy was prepared according to the method described in Example D5. The gravy was divided into two portions of 500 ml each. To the first portion were added 250 mg of the flavour powder prepared according to the method described in Example C5 and to the second portion were added 12.5 mg of 4-hydroxy-5-methyl-2,3-dihydrofuran-3-one. Both gravies were assessed in a paired comparison test by a panel consisting of 16 expert tasters. The gravy containing the flavour powder was preferred by 12 out of 16 persons because of its more pronounced fried-meat flavour.

EXAMPLE D13

A mixture of 1.0 g of 4-acetoxy-5-methyl-2,3-dihydrofuran-3-one, 2.0 g of thioacetamide and 20 ml of water were heated together in a round-bottomed flask at 100° C. for 4 hours. The reaction mixture was then allowed to cool. It had a good roast-beef flavour and was considered as a favourable additive to a beef soup prepared according to Example D8.

EXAMPLE D14

One liter of goulash soup was prepared according to Example D1. To this soup were added 1.2 mgr of 2,5-dimethyl-4-mercapto-2,3-dihydrofuran-3-one (cf. Example A9) and compared with the soup without added flavour. The addition of 2,5-dimethyl-4-mercapto-2,3-dihydrofuran-3-one gave this soup a more pronounced fuller meaty taste.

EXAMPLE D15

Two liters of gravy prepared according to Example D2 were divided into two portions of 1 liter and to the first portion were added 0.5 ml of ethanol and to the second portion 2.75 mgr of 2,5-dimethyl-4-mercaptotetrahydrofuran-3-one (cf. Example A10) dissolved in 0.5 ml of ethanol.

Both gravies were compared by a panel consisting of 25 persons. the gravy containing 2,5-dimethyl-4-mercaptotetrahydrofuran-3-one was preferred by 18 persons. The reason of the preference was its stronger more fried meat-like flavour.

What is claimed is:

1. A compound of the formula:

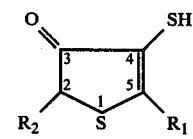

wherein $R_1$ and $R_2$ are selected from the group consisting of hydrogen, methyl and ethyl, wherein $R_1$ and $R_2$ cannot both be hydrogen simultaneously.

2. A compound according to claim 1, wherein one of $R_1$ and $R_2$ is hydrogen.

3. A compound according to claim 2, in which $R_1$ represents a methyl group.

4. A compound according to claim 2, in which $R_2$ represents a methyl group.

* * * * *